United States Patent

Fukuda et al.

Patent Number: 5,843,339
Date of Patent: Dec. 1, 1998

[54] PHOSPHITES AND THEIR PRODUCTION AND USE

[75] Inventors: Kanako Fukuda, Osaka; Naoki Inui, Nara, both of Japan

[73] Assignee: Sumitomo Chemical Company, Limited, Osaka, Japan

[21] Appl. No.: 723,933

[22] Filed: Oct. 1, 1996

[30] Foreign Application Priority Data

Oct. 2, 1995 [JP] Japan .................................. 7-254858

[51] Int. Cl.⁶ .................................................. C07D 9/6571
[52] U.S. Cl. .................... 252/400.24; 524/117; 524/128; 524/336; 524/340; 558/85; 558/87
[58] Field of Search ...................... 252/400.24; 524/117, 524/128, 336, 340; 558/85, 87

[56] References Cited

U.S. PATENT DOCUMENTS

| | | | |
|---|---|---|---|
| 3,907,939 | 9/1975 | Robin et al. | 260/953 |
| 4,252,750 | 2/1981 | Buysch et al. | 260/927 R |
| 4,351,759 | 9/1982 | Spivack | 524/100 |
| 4,668,651 | 5/1987 | Billig et al. | 502/158 |
| 5,292,785 | 3/1994 | Pastor et al. | 524/117 |
| 5,391,799 | 2/1995 | Pastor et al. | 558/96 |
| 5,576,365 | 11/1996 | Fukuda et al. | 524/117 |
| 5,616,767 | 4/1997 | Enlow et al. | 558/92 |
| 5,643,985 | 7/1997 | Hoffmann et al. | 524/291 |

FOREIGN PATENT DOCUMENTS

| | | |
|---|---|---|
| 0 250 367 A2 | 12/1987 | European Pat. Off. . |
| 0 250 367 A3 | 12/1987 | European Pat. Off. . |
| 0 617 041 A1 | 9/1994 | European Pat. Off. . |
| 5-86084 | 4/1993 | Japan . |
| 6-321975 | 11/1994 | Japan . |
| 8-208885 | 8/1996 | Japan . |

OTHER PUBLICATIONS

Chemical Abstracts, vol. 119, No. 11, (13 Sep. 1993), Abstract No. 117545.

*Primary Examiner*—Joseph K. McKane
*Assistant Examiner*—Deanna Baxam
*Attorney, Agent, or Firm*—Pillsbury Madison & Sutro LLP

[57] ABSTRACT

Phosphites represented by the general formula (I):

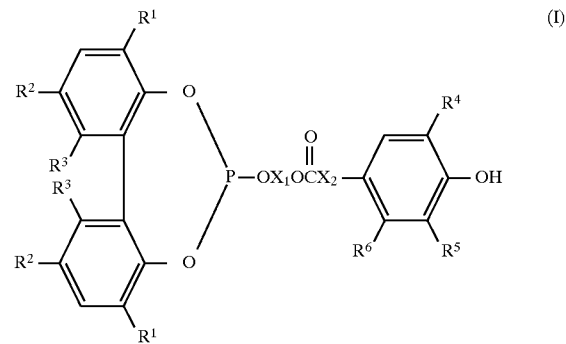

wherein $R^1$, $R^2$, $R^4$ and $R^5$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ and $R^6$ independently represent a hydrogen atom or an alkyl group having 1 to 8 carbon atoms; $X_1$ is a dihydric alcohol residue, wherein HO—$X_1$—OH defines the corresponding dihydric alcohol from which residue $X_1$, is obtained; and $X_2$ is a direct bond or an alkylene group having 1 to 8 carbon atoms; and the phosphites are useful as stabilizers for organic materials.

8 Claims, No Drawings

PHOSPHITES AND THEIR PRODUCTION AND USE

BACKGROUND OF THE INVENTION

1. Field of the Invention

The present invention relates to novel phosphites and a process for producing them and their use as stabilizer for organic material.

2. Description of the Related Art

It has been known that organic material such as thermoplastic resin, thermosetting resin, natural or synthetic rubber, mineral oil, lubricating oil, adhesive and paint are deteriorated on production, processing and use due to the action of heat, oxygen, etc., and accompanying phenomena such as molecular cleavage and molecular crosslinking. These deteriorations result in drastic damage of a commercial value. It has hitherto been known that organic materials are stabilized by containing a phenolic antioxidant, a phosphorous antioxidant, or the like, so as to solve these problems such as heat deterioration and oxidative deterioration.

As the phosphorous antioxidant, for example, distearyl pentaerythritol diphosphite, tris(2,4-di-t-butylphenyl) phosphite, bis(2,4-di-t-butylphenyl)pentaerythritol diphosphite or bis(2,6-di-t-butyl-4-methylphenyl) pentaerythritol diphosphite are used.

However, these known phosphorous antioxidants had a problem that a stabilizing effect to heat deterioration and oxidative deterioration is insufficient. There is also a problem that bis(2,4-di-t-butylphenyl)pentaerythritol diphosphite or the like is liable to be hydrolyzed and it is hydrolyzed during preservation. As a result, unevenness of processing stability arises and an organic material having a stable quality cannot be obtained. Further, there is a problem that the phosphite produced by the hydrolysis corrodes a metal in a processing machine.

On the other hand, the present inventors have already proposed an eight-membered ring phosphite such as 2-[3-(3-t-butyl-4-hydroxy-5-methylphenyl)propionyloxy]ethyl 2,2'-methylenebis(6-t-butyl-4-methylphenyl)phosphite, etc. as means for solving these problems of the phosphorous antioxidant (JP-A-5-86084). The eight-membered ring phosphite such as 2-[2-(4,8-di-t-butyl-2,10-dimethyl-12H-dibenzo[d,g][1,3,2] dioxaphosphosin-6-yl)oxy-3-t-butyl-5-methylbenzyl]-6-t-butyl-4-methylphenol, etc. is also known as a preservation stabilizer for organic isocyanate (JP-A-6-321975).

However, the stabilizing effect of these eight-membered ring phosphates to heat deterioration and oxidative deterioration is not necessarily sufficient, and it is desirable to develop an improved antioxidant.

The present inventors have produced various phosphorous compounds and studied intensively about them so as to develop an antioxidant which exhibits a more excellent effect to heat deterioration and oxidative deterioration of the organic material. Thus, the present invention has been accomplished.

SUMMARY OF THE INVENTION

It is one object of the present invention to provide novel phosphites.

It is another object of the present invention to provide a process for producing the phosphites.

It is still another object of the present invention to provide the use of the phosphites as stabilizers for organic materials. These and other objects are met by the discovery of specific cyclic phosphites, such as seven-membered ring phosphites, which exhibit excellent antioxidant properties.

DETAILED DESCRIPTION OF THE INVENTION

The present invention provides a phosphite of formula (I):

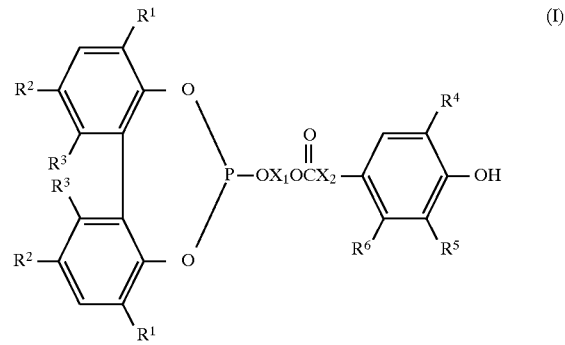

wherein $R^1$, $R^2$, $R^4$ and $R^5$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ and $R^6$ independently represent a hydrogen atom or an alkyl group having 1 to 8 carbon atoms; $X_1$ is a dihydric alcohol residue; and $X_2$ is a direct bond or an alkylene group having 1 to 8 carbon atoms, a process for producing them and their use.

In the phosphites represented by the formula (I) of the present invention, the substituents $R^1$, $R^2$, $R^4$ and $R^5$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group.

Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Examples of the cycloalkyl group having 5 to 8 carbon atoms include cyclopentyl, cyclohexyl, cycloheptyl and cyclooctyl. Examples of the alkylcycloalkyl group having 6 to 12 carbon atoms include 1-methylcyclopentyl, 1-methylcyclohexyl and 1-methyl-4-i-propylcyclohexyl. Examples of the aralkyl group having 7 to 12 carbon atoms include benzyl, α-methylbenzyl and α,α-dimethylbenzyl.

It is preferred that $R^1$ is a t-alkyl group such as t-butyl, t-pentyl and t-octyl. It is preferred that $R^2$ is an alkyl group having 1 to 5 carbon atoms such as methyl, ethyl, n-propyl, i-propyl, n-butyl, i-butyl, sec-butyl, t-butyl and t-pentyl, particularly t-butyl. It is preferred that $R^4$ and $R^5$ independently represent an alkyl group having 1 to 5 carbon atoms such as methyl, ethyl, n-propyl, i-propyl, n-butyl, i-butyl, sec-butyl, t-butyl and t-pentyl or t-alkyl group such as t-butyl, t-pentyl and t-octyl. More preferably, one of $R^4$ and $R^5$ is a t-alkyl group, particularly t-butyl group, and another is an alkyl group having 1 to 5 carbon atoms, particularly a methyl or t-butyl group.

The substituents $R^3$ and $R^6$ independently represent a hydrogen atom or an alkyl group having 1 to 8 carbon atoms. Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl. Preferably, $R^3$ and $R^6$ are hydrogen atom or alkyl group having 1 to 5 carbon atoms, particularly preferably hydrogen atom or methyl group.

The substituent $X_1$ is a dihydric alcohol residue, wherein $HO-X_1-OH$ defines the corresponding dihydric alcohol from which residue $X_1$ is obtained. Typical examples thereof include residues of alkylenediols, preferably containing 2 to 16 carbon atoms, such as ethylene glycol, 1,2-propanediol, 1,3-propanediol, 1,2-butanediol, 1,3-butanediol, 1,4-butanediol, 2,3-butanediol, 2-methyl-1,3-propanediol, 1,2-pentanediol, 1,5-pentanediol, 2,4-pentanediol, neopentyl glycol, 1,2-hexanediol, 1,5-hexanediol, 1,6-hexanediol, 2,5-hexanediol, 2-methyl-2,4-pentanediol, 2-methyl-1,5-pentanediol, 3,3-dimethylbutanediol, 2,3-dimethyl-2,3-butanediol, 2-ethyl-2-methyl-1,3-propanediol, 2,2-diethyl-1,3-propanediol, 2,4-dimethyl-2,4-pentanediol, 1,2-octanediol, 1,8-octanediol, 2,5-dimethyl-2,5-hexanediol, 2-ethyl-1,3-hexanediol, 2,2,4-trimethyl-1,3-pentanediol, 1,9-nonanediol, 2-butyl-2-ethyl-1,3-propanediol, 1,2-decanediol, 1,10-decanediol, 1,12-dodecanediol, 1,2-tetradecanediol, 1,14-tetradecanediol, 1,2-hexadecanediol and 1,16-hexadecanediol; residues of diols having a double bond, preferably containing 4 to 8 carbon atoms, such as 2-butene-1,4-diol, 2-methylene-1,3-propanediol, 5-hexene-1,2-diol and 7-octene-1,2-diol; residues of cyclic diols, preferably containing 5 to 15 carbon atoms, such as 1,2-cyclopentanediol, 1,3-cyclopentanediol, 1,2-cyclohexanediol, 1,3-cyclohexanediol, 1,4-cyclohexanediol, 1,2-cyclooctanediol, 1,4-cyclooctanediol, 1,5-cyclooctanediol, p-menthane-3,8-diol and 4,4'-isopropylidenedicyclohexanol; and residues of diols having one or more hetero atoms in addition to the oxygen atoms of the alcohol moieties, such as diethylene glycol, triethylene glycol 3,9-bis(1,1-dimethyl-2-hydroxyethyl)-2,4,8,10-tetraoxaspiro[5,5]undecane, neopentyl glycol hydroxypivalate, 2,2'-thiodiethanol, 2-methylthio-1,2-propanediol and diethanolamine. $X_1$ is preferably a residue of an alkylenediol containing 2 to 4 carbon atoms, particularly ethylene glycol.

The substituent $X_2$ is a direct bond or an alkylene group having 1 to 8 carbon atoms, and examples of the alkylene group include ethylene, propylene, butylene, pentamethylene, hexamethylene, octamethylene and 2,2-dimethyl-1,3-propylene. $X_2$ is preferably a direct bond or an alkylene group having 1 to 4 carbon atoms, particularly ethylene.

The phosphite of formula (I) can be produced, for example, by reacting a biphenol of formula (II):

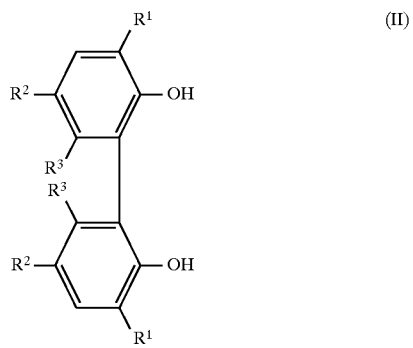

wherein $R^1$, $R^2$ and $R^3$ are as defined above, and a phosphorus trihalide with an alcohol represented by the general formula (III):

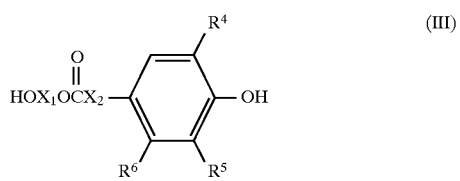

wherein $R^4$, $R^5$, $R^6$, $X_1$ and $X_2$ are as defined above, in the presence of a dehydrohalogenating agent.

Examples of the phosphorus trihalide used herein include phosphorus trichloride and phosphorus tribromide. Among them, phosphorus trichloride is preferably used.

Examples of the dehydrohalogenating agent include amines, pyridines and pyrrolidines.

The amines may be primary amine, secondary amine and tertiary amine, and examples thereof include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferred.

Examples of the pyridines include pyridine and picoline. Among them, pyridine is preferred. Examples of the pyrrolidines include 1-methyl-2-pyrrolidine.

Among these dehydrohalogenating agents, triethylamine and pyridine are preferably used.

The reaction is normally conducted in an organic solvent. The organic solvent may be any one which does not inhibit the reaction and is not specifically limited. Examples thereof include aromatic hydrocarbons aliphatic hydrocarbons oxygen-containing hydrocarbons and hydrocarbon halides.

Examples of the aromatic hydrocarbons include benzene, toluene and xylene. Examples of the aliphatic hydrocarbons include n-hexane, n-heptane and n-octane. Examples of the oxygen-containing hydrocarbons include diethyl ether and tetrahydrofuran. Examples of the hydrocarbon halides include chloroform, carbon tetrachloride, monochlorobenzene, dichloromethane, 1, 2-dichloroethane and dichlorobenzene.

Among them, toluene, xylene, diethyl ether, tetrahydrofuran and dichloromethane are preferably used.

As the reaction process, a two-stage reaction process comprising firstly reacting a biphenol (II) with a phosphorus trihalide in the presence of a dehydrohalogenating agent to form an intermediate, followed by reacting with an alcohol compound (III) is normally employed.

In case of this process, the phosphorus trihalide is preferably used in an amount within the range from about 1 to 1.1 mol, more preferably from about 1 to 1.05 mol, per mol of the biphenol (II).

The dehydrohalogenating agent is preferably used in an amount within the range from about 2 to 2.4 mol, more preferably from about 2 to 2.1 mol, per mol of the phosphorus trihalide.

The reaction between the bisphenol (II) and phosphorous trihalide is normally conducted at about 0° to 150° C. It is considered that halogenophosphite as the intermediate is produced by this reaction. The reaction mixture may be subjected to the following reaction after isolating halogenophosphite, but is normally subjected to the reaction with the alcohol (III) as it is.

When reacting with the alcohol (III), the alcohol (III) is normally used in an amount within the range from about 1 to 1.1 mol per mol of the biphenol (II).

It is preferred to additionally add the dehydrohalogenating agent in this reaction. An amount of the dehydrohalogenating agent added additionally is preferably within the range from about 1 to 1.2 mol per mol of the alcohol (III). When the excess dehydrohalogenating agent is used in the first reaction, the amount of the dehydrohalogenating agent added additionally is calculated taking the amount of the dehydrohalogenating agent remaining into consideration.

The reaction is normally conducted at about 100° to 150° C. This reaction is preferably conducted under reflux.

After the completion of the reaction, a hydrogen halide of the dehydrohalogenating agent produced by the reaction is removed. Then, after removing the solvent, the resultant is subjected to a suitable additional treatment such as crystallization or column chromatography, to obtain the phosphite (I) of the present invention.

The biphenols (II) as the raw material of the phosphites (I) can also be produced by condensing alkylphenols according to a known process, for example, process described in JP-A-2-47451. It is also possible to use commercially available biphenols (II).

The alcohols (III) as another raw material can be produced, for example, by reacting phenylcarboxylic acids represented by the general formula (IV):

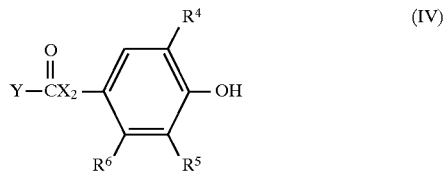

wherein $R^4$, $R^5$, $R^6$ and $X_2$ are as defined above; and Y is a lower alkoxy group having about 1 to 4 carbon atoms, a hydroxyl group or a halogen atom, with a dihydric alcohol represented by the formula HO—$X_1$—OH, wherein $X_1$ is as defined above, according to a known process.

When Y of the phenylcarboxylic acids (IV) is a lower alkoxy group, there can be used an operation comprising dissolving the phenylcarboxylic acids (IV) and dihydric alcohol in about an equimolar amount with heating, adding a small amount of a basic catalyst and heating and allowing the reaction to proceed while distilling off the resultant monohydric lower alcohol. The reaction normally proceeds at a temperature within the range from about 100° to 180° C. After completion of the reaction, alcohols (III) can be obtained by optionally subjecting to an operation comprising adding a solvent to dilute the reaction product, neutralizing the resultant solution with an acid such as acetic acid, washing the solution with water, distilling off the solvent and purifying the residue by column chromatography.

In this reaction, the dihydric alcohol is normally used in an amount of 1 mol or more, preferably within the range from about 1 to 1.2 mol, per mol of the phenylcarboxylic acids (IV).

As the basic catalyst, for example, there can be used organic alkali metal compounds such as sodium methoxide, lithium methoxide and lithium amide; and hydroxides or oxides of alkali or alkaline earth metals such as calcium oxide, sodium hydroxide, lithium hydroxide and potassium hydroxides. The basic catalyst is normally used in an amount within the range from about 0.1 to 0.2 mol per mol of the phenylcarboxylic acids (IV).

As the diluent solvent, there can be used, for example, aromatic hydrocarbons, aliphatic hydrocarbons, alcohols or ethers. Normally, aromatic hydrocarbons are preferred and specific examples thereof include toluene, xylene and monochlorobenzene.

The phosphites (I) of the present invention are useful for stabilizing heat deterioration and oxidative deterioration of organic materials. Examples of the organic material which can be stabilized by the present invention include the following. Also, a mixture of two or more of the following organic materials can be stabilized.

(1) Polyethylene, such as high-density polyethylene (HD-PE), low-density polyethylene (LD-PE), linear low-density polyethylene (LLDPE).
(2) Polypropylene
(3) Methylpentene polymer
(4) EEA (ethylene-ethyl acrylate copolymer) resin
(5) Ethylene-vinyl acetate copolymer resin
(6) Polystyrenes, such as polystyrene, poly(p-methylstyrene), poly(α-methylstyrene)
(7) AS (acrylonitrile-styrene copolymer) resin
(8) ABS (acrylonitrile-butadiene-styrene copolymer) resin
(9) AAS (acrylic rubber-acrylonitrile-styrene copolymer) resin
(10) ACS (acrylonitrile-chlorinated polyethylene-styrene copolymer) resin
(11) Chlorinated polyethylene, polychloroprene, chlorinated rubber
(12) Polyvinyl chloride, polyvinylidene chloride
(13) Methacrylic resin
(14) Ethylene-vinyl alcohol copolymer resin
(15) Fluororesin
(16) Polyacetal
(17) Grafted polyphenylene ether resin and polyphenylene sulfide resin
(18) Polyurethane
(19) Polyamide
(20) Polyethylene terephthalate, polybutylene terephthalate
(21) Polycarbonate
(22) Polyacrylate
(23) Polysulfone, polyether ether ketone, polyether sulfone
(24) Thermoplastic resin such as aromatic polyester
(25) Epoxy resin
(26) Diallyl phthalate prepolymer
(27) Silicone resin
(28) Unsaturated polyester resin
(29) Acryl-modified benzoguanamine resin
(30) Benzoguanamine-melamine resin
(31) Thermosetting resin such as urea resin
(32) Polybutadiene
(33) 1,2-Polybutadiene
(34) Polyisoprene
(35) Styrene-butadiene copolymer
(36) Butadiene-acrylonitrile copolymer
(37) Ethylene-propylene copolymer
(38) Silicone rubber
(39) Epichlorohydrin rubber
(40) Acrylic rubber
(41) Natural rubber
(42) Chlorine rubber paint
(43) Polyester resin paint
(44) Urethane resin paint
(45) Epoxy resin paint
(46) Acrylic resin paint
(47) Vinyl resin paint
(48) Aminoalkyd resin paint
(49) Alkyd resin paint
(50) Nitrocellulose resin paint
(51) Oil paint
(52) Wax
(53) Lubricant oil The phosphites are preferably used for the thermoplastic resin. Particularly polyolefins such as polyethylene including HD-PE, LD-PE and LLDPE and polypropylene are preferably used.

When the phosphites (I) of the present invention are added to stabilize the organic material, the phosphites (I) are preferably added in an amount within the range from about 0.01 to 2 parts by weight based on 100 parts by weight of the organic material. When the amount used is less than 0.01 parts by weight, the stabilizing effect is not necessarily sufficient. On the other hand, when the amount exceeds 2 parts by weight, an additional effect corresponding to the amount in excess of 2 parts by weight is not obtained, and it is economically disadvantageous.

There can be optionally formulated other additives such as phenolic antioxidants, sulfur antioxidants, phosphorous antioxidants, ultraviolet absorbers, hindered amine photostabilizers, lubricants, plasticizers, flame retardants, nucleating agents, metal deactivators, antistatic agents, pigments, inorganic fillers, antiblocking agents and neutralizing agents (e.g. calcium stearate or hydrotalcite.) in the organic material wherein the phosphites (I) of the present invention are contained. They can be formulated in the same stage where the phosphites (I) are formulated. It is also possible to formulate them in a different stage from that where the phosphites (I) are formulated. Thus the present invention provides a stabilizer for organic material comprising a phosphite (I) as an active ingredient and optionally further comprising one or more of the above additives.

Examples of the phenolic antioxidant include the following:

n-octadecyl 3-(3,5-di-t-butyl-4-hydroxyphenyl) propionate,
pentaerythrityl tetrakis[3-(3,5-di-t-butyl-4-hydroxyphenyl) propionate],
triethylene glycol bis[3-(3,5-di-t-butyl-4-hydroxyphenyl) propionate]
3,9-bis[2-(3-(3-t-butyl-4-hydroxy-5-methylphenyl) propionyloxy)-1,1-dimethylethyl]-2,4,8,10-tetraoxaspiro[5,5]undecane,
tris(4-t-butyl-3-hydroxy-2,6-dimethylbenzyl)isocyanurate,
2,2'-ethylidenebis(4,6-di-t-butylphenol),
2,2'-methylenebis(4-methyl-6-t-butylphenol),
4,4'-thiobis(3-methyl-6-t-butylphenol),
4,4'-butylidenenebis(3-methyl-6-t-butylphenol), and
2,6-di-t-butyl-4-methylphenol).

Examples of the sulfur antioxidant include the following:
dilauryl 3,3'-thiodipropionate,
dimyristyl 3,3'-thiodipropionate,
distearyl 3,3'-thiodipropionate,
lauryl stearyl 3,3'-thiodipropionate, and
pentaerythrityl tetrakis(3-laurylpropionate).

Examples of the ultraviolet absorber include the following:
2-hydroxy-4-methoxybenzophenone,
2-hydroxy-4-octoxybenzophenone,
2,2'-dihydroxy-4-methoxybenzophenone,
bis(5-benzoyl-4-hydroxy-2-methoxyphenyl)methane,
2,2',4,4'-tetrahydroxybenzophenone,
2-(2-hydroxy-5-methylphenyl)benzotriazole,
2-[2-hydroxy-3-(3,4,5,6-tetrahydrophthalimidemethyl)-5-methylphenyl]benzotriazole,
2-(3-t-butyl-2-hydroxy-5-methylphenyl)-5-chlorobenzotriazole,
2-(2-hydroxy-5-t-octylphenyl)benzotriazole,
2-(3,5-di-t-butyl-2-hydroxyphenyl)benzotriazole,
2-(3,5-di-t-amyl-2-hydroxyphenyl)benzotriazole,
2-(3,5-di-t-butyl-2-hydroxyphenyl)-5-chlorobenzotriazole,
2-[2-hydroxy-3,5-bis(α, α-dimethylbenzyl)phenyl]-2H-benzotriazole,
2,2'-methylenebis[6-(2H-benzotriazol-2-yl)-4-(1,1,3,3-tetramethylbutyl)phenol],
2,2'-methylenebis[4-t-butyl-6-(2H-benzotriazol-2-yl) phenol],
condensate of poly(3–11) (ethylene glycol) with methyl 3-[3-(2H-benzotriazol-2-yl)-5-t-butyl-4-hydroxyphenyl] propionate,
2-ethylhexyl 3-[3-t-butyl-5-(5-chloro-2H-benzotriazol-2-yl)-4-hydroxyphenyl]propionate,
octyl 3-[3-t-butyl-5-(5-chloro-2H-benzotriazol-2-yl)-4-hydroxyphenyl]propionate,
methyl 3-[3-t-butyl-5-(5-chloro-2H-benzotriazol-2-yl)-4-hydroxyphenyl]propionate, and
3-[3-t-butyl-5-(5-chloro-2H-benzotriazol-2-yl)-4-hydroxyphenyl] propionic acid.

Examples of the hindered amine photostabilizer include the following:
bis(2,2,6,6-tetramethyl-4-piperidyl)sebacate,
bis(1,2,2,6,6-pentamethyl-4-piperidyl) 2-(3,5-di-t-butyl-4-hydroxybenzyl)-2-butylmalonate,
bis(1-acrolyl-2,2,6,6-tetramethyl-4-piperidyl) 2,2-bis(3,5-di-t-butyl-4-hydroxybenzyl)-2-butylmalonate,
bis(1,2,2,6,6-pentamethyl-4-piperidyl)decanedioate,
bis(2,2,6,6-tetramethyl-4-piperidyl)succinate,
2,2,6,6-tetramethyl-4-piperidyl methacrylate,
4-[3-(3,5-di-t-butyl-4-hydroxyphenyl)propionyloxy]-1-[2-(3-(3,5-di-t-butyl-4-hydroxyphenyl) propionyloxy)ethyl]-2,2,6,6-tetramethylpiperidine,
2-methyl-2-(2,2,6,6-tetramethyl-4-piperidyl)amino-N-(2,2,6,6-tetramethyl-4-piperidyl)propionamide,
tetrakis(2,2,6,6-tetramethyl-4-piperidyl)-1,2,3,4-butanetetracarboxylate,
tetrakis(1,2,2,6,6-pentamethyl-4-piperidyl)-1,2,3,4-butanetetracarboxylate,
mixed esterified product of 1,2,3,4-butanetetracarboxylic acid with 1,2,2,6,6-pentamethyl-4-piperidinol and 1-tridecanol,
mixed esterified product of 1,2,3,4-butanetetracarboxylic acid with 2,2,6,6-tetramethyl-4-piperidinol and 1-tridecanol,
mixed esterified product of 1,2,3,4-butanetetracarboxylic acid with 1,2,2,6,6-pentamethyl-4-piperidinol and 3,9-bis(2-hydroxy-1,1-dimethylethyl)-2,4,8,10-tetraoxaspiro[5,5]undecane,
mixed esterified product of 1,2,3,4-butanetetracarboxylic acid with 2,2,6,6-tetramethyl-4-piperidinol and 3,9-bis(2-hydroxy-1,1-dimethylethyl)-2,4,8,10-tetraoxaspiro[5,5] undecane,
polycondensate of dimethyl succinate with 1-(2-hydroxyethyl)-4-hydroxy-2,2,6,6-tetramethylpiperidine,
poly[(6-morpholino-1,3,5-triazin-2,4-diyl)((2,2,6,6-tetramethyl-4-piperidyl) imino)hexamethylene((2,2,6,6-tetramethyl-4-piperidyl) imino)],
poly[(6-(1,1,3,3-tetramethylbutyl)imino-1,3,5-triazin-2,4-diyl)((2,2,6,6-tetramethyl-4-piperidyl) imino) hexamethylene ((2,2,6,6-tetramethyl-4-piperidyl)imino)],
polycondensate of N,N'-bis(2,2,6,6-tetramethyl-4-piperidyl) hexamethylenediamine with 1,2-dibromoethane,
N,N'-4,7-tetrakis[4,6-bis(N-butyl-N-(2,2,6,6-tetramethyl-4-piperidyl)amino)-1,3,5-triazin-2-yl]-4,7-diazadecane-1,10-diamine,
N,N'-4,7-tris[4,6-bis(N-butyl-N-(2,2,6,6-tetramethyl-4-piperidyl)amino)-1,3,5-triazin-2-yl]-4,7-diazadecane-1,10-diamine,
N,N'-4,7-tetrakis[4,6-bis(N-butyl-N-(1,2,2,6,6-pentamethyl-4-piperidyl)amino)-1,3,5-triazin-2-yl]-4,7-diazadecane-1,10-diamine, and
N,N'-4-tris[4,6-bis(N-butyl-N-(1,2,2,6,6-pentamethyl-4-piperidyl )amino) -1,3,5-triazin-2-yl]-4,7-diazadecane-1,10-diamine.

For formulating the phosphites (I) or other additives used optionally to the organic material, there can be used any known process and device for obtaining a uniform mixture. For example, when the organic material is a solid polymer, the phosphites (I) and optional other additives can be directly dry-blended with the solid polymer. Alternatively, the phosphite compounds and optional other additives can be formulated to the solid polymer in the form of a master batch. When the organic material is a polymer solution or a liquid polymer, the phosphites (I) and optional other additives can also be formulated to the polymer solution or a liquid polymer on or immediately after polymerization in the form of a solution or dispersion. On the other hand, when the organic material is a liquid such as oil, the phosphites (I) and optional other additives can also be directly added and dissolved. Alternatively, the phosphites (I) and optional other additives can also be added in the state of being dissolved or dispersed in a liquid solvent.

The phosphites (I) of the present invention have an excellent performance as stabilizers for various organic materials including thermoplastic resins, and organic materials containing a phosphite (I) are stable to heat deterioration and oxidative deterioration on production, processing and use and are high-quality products.

The following Examples further illustrate the present invention in detail but are not to be construed to limit the scope thereof.

EXAMPLE 1

Production of 3-(3-t-butyl-4-hydroxy-5-methylphenyl) propionic acid 2-[(2,4,8,10-tetra-t-butyldibenzo[d,f][1,3,2] dioxaphosphepin-6-yl)oxy]ethyl (compound 1)

In a 500 ml four-necked flask equipped with a thermometer, a stirrer and a condenser, 18.8 g of 3,3',5,5'-tetra-t-butyl biphenyl-2,2'-diol and 94.5 g of triethylamine were charged. After the inside of the container was substituted with nitrogen, 6.2 g of phosphorus trichloride was added dropwise with stirring. After the completion of the addition, the mixture was maintained at 80° C. for 3 hours and cooled to room temperature. Then, 4.75 g of triethylamine and a solution prepared by dissolving 12.7 g of 3-(3-t-butyl-4-hydroxy-5-methylphenyl)propionic acid 2-hydroxyethyl in 50 ml of anhydrous toluene were charged, followed by maintaining under reflux for 6 hours. After cooling to room temperature, the resultant hydrochloride of triethylamine was filtered. The filtrate was concentrated, and then the residue was purified by subjecting to silica gel column chromatography to obtain 20.6 g of a colorless crystal.

Mass spectrometric analysis value (FD-MS): m/z 718
Melting point: 136° C.
1H-NMR(CDCl$_3$)
1.34(s, 18H), 1.39(s, 9H), 1.48(s, 18H), 2.21(s, 3H), 2.58(t, 8 Hz, 3H), 2.82(t, 8 Hz, 3H), 3.93(m, 2H), 4.11(t, 8 Hz, 3H), 6.82(t, 1 Hz, 1H), 6.94(d, 1 Hz, 1H), 7.16(d, 1 Hz, 1H), 7.41(d, 1 Hz, 1H)

EXAMPLE 2

Heat stability test of linear low-density polyethylene

| [Formulation] | |
|---|---|
| Non-stabilized linear low-density polyethylene | 100 Parts by weight |
| Hydrotalcite | 0.1 Parts by weight |
| Test compound | 0.1 Parts by weight |

KA-1: Compound 1 (produced in Example 1)
P-1: bis(2,4-di-t-butylphenyl)pentaerythritol diphosphite
P-2: tris(2,4-di-t-butylphenyl)phosphite
P-3: 2-[3-(3-t-butyl-4-hydroxy-5-methyphenyl) propionyloxy]ethyl 2,2'-methylenebis(6-t-butyl-4-methylphenyl)phosphite
P-4: 2-[2-(4,8-di-t-butyl-2,10-dimethyl-12H-dibenzo[d,g] [1,3,2]dioxaphosphosin-6-yl)oxy-3-t-butyl-5-methylbenzyl]-6-t-butyl-4-methylphenol Using a 30 mm φ mono axial extruder, the above formulation was extruded into pellets at 250° C. The resultant pellets were kneaded under a nitrogen atmosphere at 240° C., 100 rpm, using a laboplasto mill, and the time required for a torque value due to crosslinking to reach a maximum value (gel build-up time, minute) was measured. The results are shown in Table 1 as "processing stability".

The longer the gel build-up time, the more crosslinking on kneading is inhibited and the better the processing stability becomes.

Using a test compound which was allowed to stand in a thermo-hygrostat (40° C., 80%) for 7 days, the same test was conducted and the hydrolytic stability of the compound was evaluated. The results are shown in Table 1 as "hydrolysis resistance".

The processing stability of the hydrolyzed compound is deteriorated. Therefore, the better the processing stability after treatment, the better the hydrolysis resistance becomes.

The resultant pellets were press-molded at 250° C. to obtain a sheet having a thickness of 1 mm, and transparency of this sheet was visually evaluated. The results are shown in Table 1 as "dispersion properties".

The better the transparency, the better the dispersion properties in the polymer become.

In Table 1, dispersion properties are indicated according to the following criteria.

TABLE 1

| | Example No. | Comparative Example No. | | | |
|---|---|---|---|---|---|
| | 1 | 1 | 2 | 3 | 4 | 5 |
| Test compound | KA-1 | — | P-1 | P-2 | P-3 | P-4 |
| Processing stability | 21 | 5 | 7 | 7 | 16 | 15 |
| Hydrolysis resistance | 21 | — | 7 | 4 | 16 | 15 |
| Dispersion properties | ⊚ | — | X | X | ◯ | ◯ |

⊚: Good
◯: Slightly good
Δ: Slightly opaque
X: Opaque

What is claimed is:

1. A phosphite represented by the formula (I):

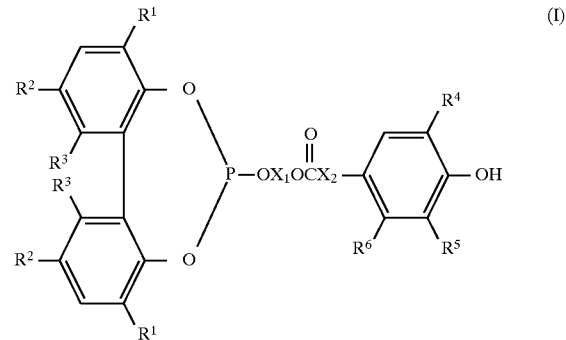

wherein $R^1$, $R^2$, $R^4$ and $R^5$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ and $R^6$ independently represent a hydrogen atom or an alkyl group having 1 to 8 carbon atoms; $X_1$ is a dihydric alcohol residue, wherein HO—$X_1$—OH defines the corresponding dihydric alcohol from which residue $X_1$ is obtained; and $X_2$ is a direct bond or an alkylene group having 1 to 8 carbon atoms.

2. A phosphite according to claim 1, wherein $R^1$ represents a t-alkyl group, $R^2$ represents an alkyl group having 1 to 5 carbon atoms, $R^4$ and $R^5$ independently represent an alkyl group having 1 to 5 carbon atoms or a t-alkyl group, and $R^3$ and $R^6$ independently represent a hydrogen atom or an alkyl group having 1 to 5 carbon atoms.

3. A phosphite according to claim 1, wherein $R^1$ represents t-butyl, t-pentyl or t-octyl, $R^2$ represents t-butyl, one of $R^4$ and $R^5$ is a t-butyl group and another is a methyl or t-butyl group, and $R^3$ and $R^6$ independently represent a hydrogen atom or a methyl group.

4. A process for producing a phosphites of claim 1, which comprises reacting a biphenol represented by the formula (II):

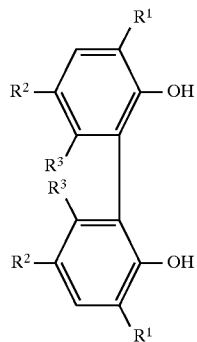

wherein $R^1$, $R^2$ and $R^3$ are as defined in claim 1, and a phosphorus trihalide with an alcohol represented by the general formula (III):

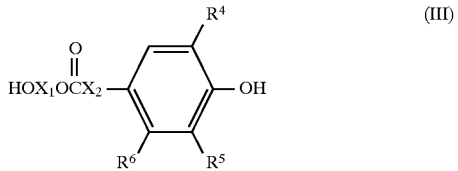

wherein $R^4$, $R^5$, $R^6$ and $X_1$ and $X_2$ are as defined in claim 1, in the presence of a dehydrohalogenating agent.

5. A stabilizer for organic material comprising a phosphites of claim 1 as an active ingredient.

6. A stabilized organic material composition comprising an organic material and a phosphites of claim 1.

7. A composition according to claim 6 wherein the organic material is a thermoplastic resin.

8. A composition according to claim 7 wherein the thermoplastic resin is a polyolefin.

* * * * *